United States Patent [19]

Nickisch et al.

[11] Patent Number: 4,804,662
[45] Date of Patent: Feb. 14, 1989

[54] SUBSTITUTED 4-(1H-IMIDAZOL-1-YL)BENZAMIDES AS ANTIARRHYTHMIC AGENTS

[75] Inventors: Klaus Nickisch, Berlin, Fed. Rep. of Germany; Randall E. Lis, Stanhope, N.J.; William C. Lumma, Jr., Pennsburg, Pa.; Thomas K. Morgan, Jr.; Ronald A. Wohl, both of Morris Plains, N.J.

[73] Assignee: Schering A.G., Berlin, Fed. Rep. of Germany

[21] Appl. No.: 46,222

[22] Filed: May 5, 1987

[51] Int. Cl.$^4$ ............... A61K 31/495; A61K 31/415; C07D 403/10
[52] U.S. Cl. ........................... 514/252; 514/218; 514/390; 514/397; 514/399; 514/400; 540/575; 540/603; 544/370; 546/276; 548/336; 548/346
[58] Field of Search ............... 544/370; 540/575, 603; 548/336, 346; 546/276; 514/218, 252, 397, 390, 399, 400

[56] References Cited

PUBLICATIONS

Inagaki et al., Image-Receiving Element for Silver Salt Diffusion.

Primary Examiner—Donald G. Daus
Assistant Examiner—Cecilia Shen
Attorney, Agent, or Firm—Elizabeth A. Bellamy; John L. White; I. William Millen

[57] ABSTRACT

Novel substituted 4-[1H-imidazol-1-yl]benzamides and their use in the treatment of cardiac arrthythmias especially as Class III or combination Class I/III antiarrhythmic agents is described. Pharmaceutical formulations containing such compounds are also disclosed.

14 Claims, No Drawings

SUBSTITUTED 4-(1H-IMIDAZOL-1-YL)BENZAMIDES AS ANTIARRHYTHMIC AGENTS

FIELD OF INVENTION

This invention relates to novel imidazole substituted benzamides and their use as antiarrhythmic agents. Specifically, this invention relates to novel substituted 4-[1H-imidazol-1-yl]benzamides and their pharmaceutically acceptable salts, to pharmaceutical compositions containing them as active ingredients. It also relates to the method of using these compounds in the treatment of arrhythmias, especially in the treatment of arrhythmias for which Class III or combination Class I/III agents are effective.

GENERAL DESCRIPTION OF THE INVENTION

Composition-of-Matter Aspect

In its composition-of-matter aspect this invention relates to novel substituted 4-[1H-imidazol-1-yl]benzamides and their pharmaceutically acceptable salts. Particularly, this invention relates to the novel compounds defined by the following formula I:

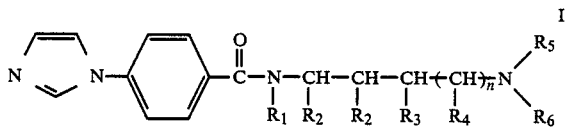

wherein $R_1$ is hydrogen, lower alkyl, lower alkenyl, lower alkoxy-lower alkyl, phenyl, substituted phenyl, naphthalenyl, substituted napthalenyl, phenylalkyl, substituted phenylalkyl or collectively with $R_5$ may produce a piperazine or a hexahydro-1,4-diazepine ring system.

$R_2$ is hydrogen, lower alkyl, phenyl, substituted phenyl, naphthalenyl, substituted naphthalenyl, collectively with $R_3$ is a bond or alkylene chain to form a saturated carbocyclic ring system of from 4 to 8 ring members or collectively with $R_5$ is an alkylene chain to form a heterocycle of from 5 to 8 ring members.

$R_3$ is hydrogen, lower alkyl, phenyl, substituted phenyl, naphthalenyl, substituted naphthalenyl, or collectively with $R_5$ is an alkylene chain to form a heterocycle of from 5 to 8 ring members.

$R_4$ is hydrogen, methyl or ethyl.

$R_5$, $R_6$ are hydrogen, lower alkenyl, $C_1$–$C_8$ straight or branched chain alkyl, $C_3$–$C_6$ cycloalkyl, cycloalkyl(lower)-alkyl, lower alkyl substituted by phenyl which may be substituted by up to 3 substituents selected from hydroxy or methoxy groups, or when taken together form a saturated heterocyclic ring of from 4 to 8 ring members which may be substituted by one or more methyl groups or optionally contains an

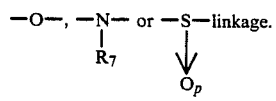

—O—, —N— or —S—linkage.

$R_7$ is a $C_1$–$C_8$ straight or branched chain alkyl or phenylalkyl wherein the phenyl group may be optionally substituted by up to 3 substituents selected from $C_1$–$C_4$ alkyl, $C_1$–$C_4$ alkoxy, trifluoromethyl, fluorine, chlorine and bromine. In this invention p is the integer 0, 1 or 2 and n is the integer 0 or 1.

This invention is inclusive of the following provisos:

(a) only one of $R_1$, $R_2$ or $R_3$ can contain an aromatic substituent, (b) if one of $R_2$ or $R_3$ contains an aromatic substitutent then the other plus $R_1$ and $R_4$ must be hydrogen, (c) $R_5$ and $R_6$ cannot both be hydrogen, (d) when any one of $R_1$, $R_5$ or $R_6$ is lower alkenyl, the unsaturation cannot be alpha to the nitrogen atom.

Also contemplated as part of this invention are the pharmaceutically acceptable salts of the compounds of Formula I. Useful acids for this purpose include inorganic acids such as hydrobromic, hydrochloric, sulfuric or phosphoric and organic acids such as acetic, propanoic, benzoic, napthalenecarboxylic, oxalic, succinic, maleic, malic, adipic, lactic, tartaric, citric, salicylic, methanesulfonic and p-toluenesulfonic.

It is to be understood that the definition of the compounds of Formula I encompasses all possible stereoisomers and mixtures thereof, which possess the activity discussed below. In particular, it encompasses racemic modifications and any optical isomers which possess the indicated activity.

In the above Formula I lower alkyl/alkoxy terms shall refer to a straight or branched chain of from 1 to 4 carbon atoms, lower alkenyl shall refer to a straight or branched chain of from 3 to 4 carbon atoms having present a double bond. The term phenylalkyl shall refer to a phenyl group at the terminus of a $C_1$–$C_4$ straight chain. The terms substituted phenyl, substituted phenylalkyl and substituted naphthalenyl shall be taken to mean phenyl or naphthalenyl moieties which may be substituted with 1 to 3 substituents selected from the group consisting of $C_1$–$C_4$ alkyl, $C_1$–$C_4$ alkoxy, trifluoromethyl, fluorine, chlorine and bromine. The term cycloalkyl(lower)alkyl shall contain 4 to 11 carbon atoms.

Preferred classes of compounds embodied by this invention are those of the above general Formula I having one of the following characteristics:

(a) where $R_5$ or $R_6$ is a $C_1$–$C_8$ straight or branched chain alkyl;

(b) where $R_2$ collectively with $R_3$ is an alkylene chain to form a saturated carbocyclic ring of from 4 to 8 carbon atoms;

(c) where one of $R_1$, $R_2$ or $R_3$ is a phenyl, substituted phenyl, naphthalenyl or substituted naphthalenyl moiety;

(d) where $R_5$ and $R_6$ are both $C_1$–$C_8$ straight or branched chain alkyl;

(e) where one of $R_1$, $R_2$ or $R_3$ is a substituted phenyl or naphthalenyl moiety.

The most preferred compounds of this invention are those having any one of the foregoing a,b,c,d or e characteristics and where n is the integer 0.

The compounds which follow are some of those which serve to exemplify various aspects of the invention described herein.

(1) N-[2-(Diethylamino)ethyl]-4-(1H-imidazol-1-yl)-benzamide.

(2) trans-N-[2-(Diethylamino)cyclohexyl]-4-(1H-imidazol-1-yl)benzamide.

(3) N-[2-(Diethylamino)ethyl]-4-(1H-imidazol-1-yl)-N-(1-naphthalenyl)benzamide.

(4) 1-[4-(1H-Imidazol-1-yl)benzoyl]-4-methylpiperazine.

(5) N-[(1-Ethylpyrrolidin-2-yl)methyl]-4-(1H-imidazol-1-yl)benzamide.
(6) 4-(1H-Imidazol-1-yl)-N-[2-[bis-(phenylmethyl)amino]ethyl]benzamide.
(7) 4-(1H-Imidazol-1-yl)-N-[2-[(phenylmethyl)amino]ethyl]benzamide.
(8) N-[2-(Diethylamino)ethyl]-4-[1H-imidazol-1-yl]-N-(4-methoxyphenyl)benzamide.
(9) N-[2-[(Diethylamino)methyl]cyclohexyl]-4-(1H-imidazol-1-yl)benzamide.
(10) N-[3-(Diethylamino)propyl]-4-(1H-imidazol-1-yl)benzamide.
(11) 4-Butyl-2,3,4,5,6,7-hexahydro-1-[4-(1H-imidazol-1-yl)benzoyl]-1,4-1H-diazepine.
(12) 4-(1H-Imidazol-1-yl)-N-[3-[pentyl(2-propenyl)amino]propyl]benzamide.
(13) N-[3-(Diethylamino)-3-methylpropyl]-4-(1H-imidazol-1-yl)benzamide.
(14) N-[2-(Diethylamino)ethyl]-4-[1H-imidazol-1-yl]-N-phenylbenzamide.
(15) N-[2-(Diethylamino)ethyl]-4-[1H-imidazol-1-yl]-N-(4-methylphenyl)benzamide.
(16) N-(4-Chlorophenyl)-N-[2-(diethylamino)ethyl]-4-(1H-imidazol-1-yl)benzamide.
(17) N-[2-(Diethylamino)ethyl]-N-(2 6-dimethylphenyl)-4-(1H-imidazol-1-yl)benzamide.
(18) N-[2-(Diethylamino)ethyl]-4-(1H-imidazol-1-yl)-N-[2,6-bis(1-methylethyl)pheny]benzamide.
(19) N-[3-Chloro-4-methoxyphenyl]-N-[2-[ethyl(heptyl)amino]ethyl]-4-(1H-imidazol-1-yl)-benzamide.
(20) N-[2-Chloro-4-methoxyphenyl]-4-(1H-imidazol-1-yl)-N-[2-[(2-propenyl)(cylohexylmethyl)amino]ethyl]benzamide.
(21) N-[4-(1,1-Dimethylethyl)phenyl]-4-(1H-imidazol-1-yl)-N-[3-(4-morpholinyl)propyl]benzamide.
(22) N-[4-Bromophenyl]-4-(1H-imidazol-1-yl)-N-[2-[(2-phenylethyl)amino]ethyl]benzamide.
(23) N-[2-(Diethylamino)-1-phenylethyl]-4-(1H-imidazol-1-yl)benzamide.
(24) N-[2-(Diethylamino)-2-(naphthalen-1-yl)ethyl]-4-(1H-imidazol-1-yl)benzamide.
(25) N-[2-(3,4-Dichlorophenyl)-3-(1-pyrrolidinyl)propyl]-4-(1H-imidazol-1-yl)benzamide.
(26) N-[2-Diethylamino-1-(3,4,5-trimethoxyphenyl)ethyl]4-(1H-imidazol-1-yl)benzamide.
(27) N-[1-(2,4-Dichlorophenyl)-2-(diethylamino)ethyl]-4-(1H-imidazol-1-yl)benzamide.
(28) N-[2-[(Cyclohexylmethyl)amino]-1-(4-trifluoromethylphenyl)ethyl]-4-(1H-imidazol-1-yl)benzamide.
(29) N-[2-(Diethylamino)ethyl]-4-(1H-imidazol-1-yl)-N-(phenylmethyl)benzamide.
(30) N-[2-(Diethylamino)cyclohexyl]-4-(1H-imidazol-1-yl)-N-(phenylmethyl)benzamide.
(31) N-[3-[Ethyl(heptyl)amino]-4-(1H-imidazol-1-yl)-N-(2-phenylethyl)benzamide.

PROCESS ASPECT

In general, the compounds of this invention may be prepared using various reactants and processes known in the art. Illustrative but not limiting as the reactants and processes utilized for the preparation of the compounds of the invention are the following Schemes A & B.

Scheme A

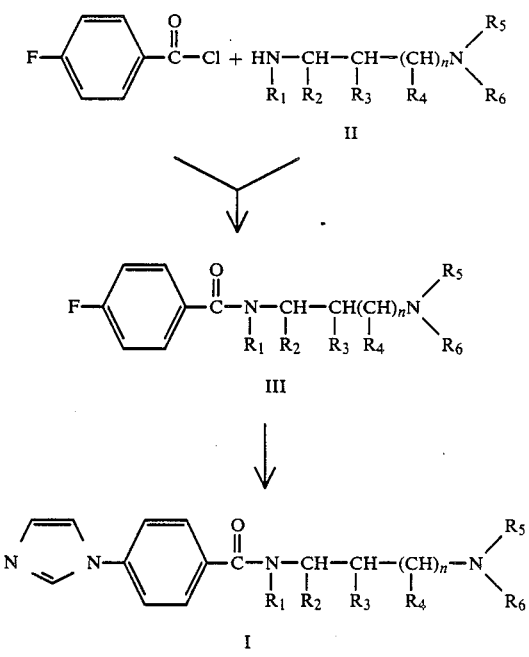

As illustrated in Scheme A, wherein $R_1$–$R_6$ and n are as previously defined, the condensation of p-fluorobenzoyl chloride with known in the art diamines (II) is accomplished in aprotic anhydrous solvents such as tetrahydrofuran, acetonitrile or methylene chloride at a temperature of from −10° C. to 50° C., preferably at about 0° C. to produce the fluorobenzamides (III).

These intermediates (III) may also be produced by the addition of p-fluorobenzoyl chloride to an aqueous sodium carbonate solution of diamines (II) at about 0° C.

The compounds of Formula I may be produced by heating a mixture of the intermediate (III) with imidazole and sodium hydride or potassium carbonate in a polar aprotic solvent such as dimethylformamide or dimethylsulfoxide at about 125° C.

Scheme B

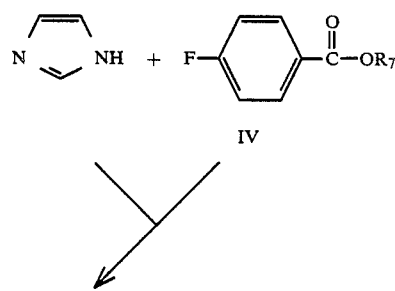

-continued
Scheme B

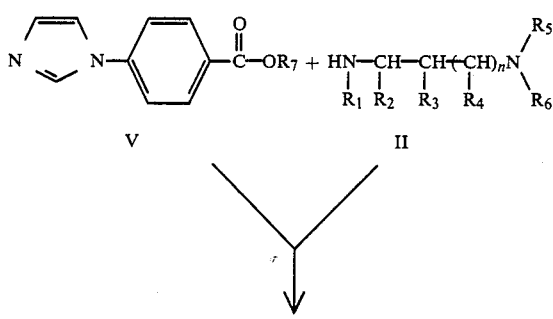

Scheme C

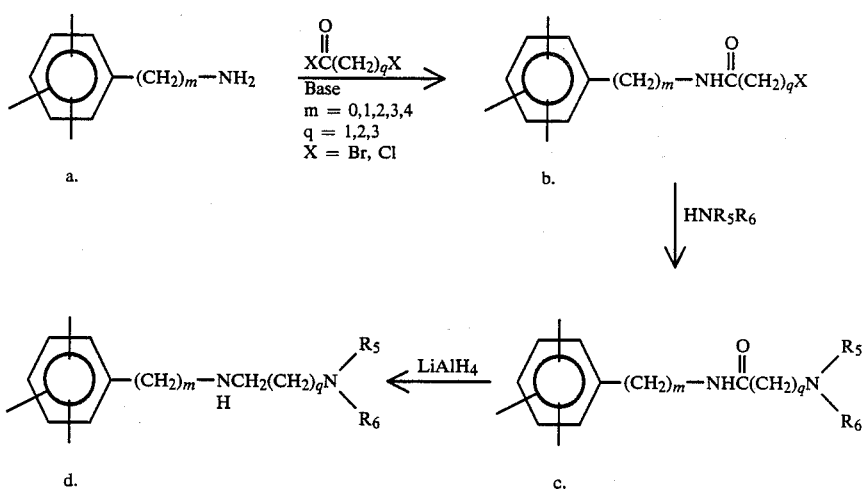

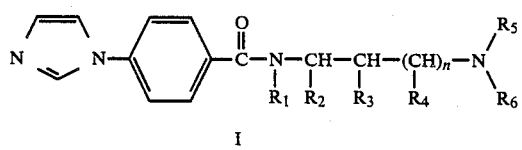

A illustrated in the foregoing Scheme B, wherein $R_1$, $R_2$, $R_3$, $R_4$, $R_5$, $R_6$ and n are as previously described and $R_7$ is methyl or ethyl, the 4-(1H-imidazol-1-yl)benzoic acid ester intermediate (V) is prepared by heating a mixture of imidazole and p-fluorobenzoic acid ester (IV) with potassium carbonate in a polar aprotic solvent such as dimethylsulfoxide at 120° C.

Said intermediate (V) is then heated with the appropriate diamine (II) either neat or in xylene at reflux to produce the compounds of Formula I. Alternatively the diamine may be activated by addition of trimethylaluminum prior to reaction with the ester (Weinreb procedure). This reaction is generally carried out in methylene chloride at reflux.

Whereas many of the diamine intermediates (II) necessary for the above Schemes A & B may be purchased or are easily prepared by methods known in the art certain others—especially those where one of $R_1$, $R_2$ or $R_3$ contains an aryl moiety are prepared as follows.

In the following Schemes C-F it should be noted that where anilines, arylalkylamines, acetophenones and phenylacetonitriles are shown as starting materials, the corresponding naphthylamines, naphthlalkylamines, acetonaphthones and naphthylacetonitriles may also be employed.

The route outlined in the foregoing Scheme C illustrates the preparation of the intermediate amines of the invention wherein $R_1$ is aryl or arylalkyl and $R_2$, $R_3$ and $R_4$ are hydrogen. An appropriately substituted aniline or arylalkylamine (a) is reacted with an ω-halo (chloro or bromo) acetyl or propionyl halide (chloride or bromide) in a solvent such as methylene chloride or acetic acid in the presence of a base such as pyridine, triethylamine or sodium acetate at a temperature of from about $-20°$ C. to about 50° C. preferably at 0°–20° C. The resulting ω-haloacylanilide or N-(arylalkyl)-ω-haloacetamide (b) is then reacted with a secondary amine either neat or in a solvent such as water or a lower alkanol at a temperature from 20° C. to about 120° C. preferably from about 25° C. to 50° C. to yield (c). In the instance wherein one of $R_5$ or $R_6$ in the final product is hydrogen, then the foregoing secondary amine will have as one of its substituents a suitable N-protecting group such as benzyl or 4-methoxybenzyl. Said protecting group can be easily removed as the very last step of the synthesis. The compound (c) is reduced with lithium aluminum hydride in a solvent such as diethyl ether or tetrahydrofuran at a temperature of from 20° C. to 100° C. preferably at 60°–80° C. to provide the N-aryldiamine or N-arylalkyldiamine (d).

Scheme D

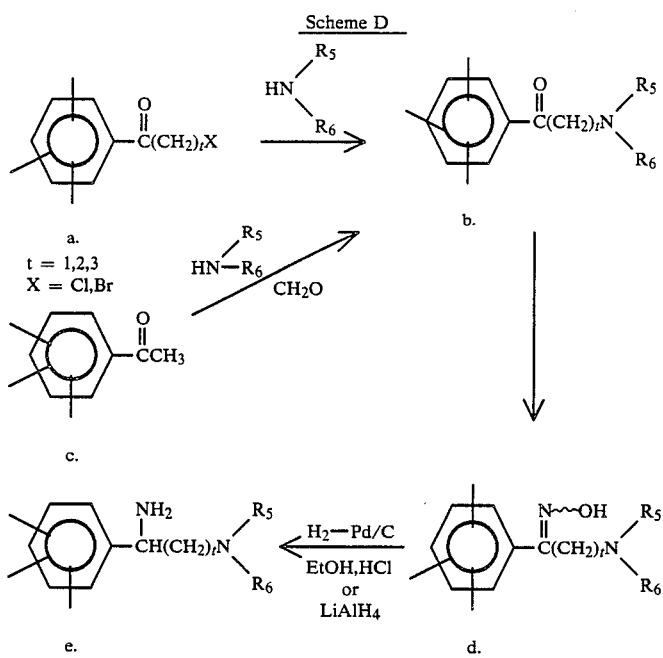

a.
t = 1,2,3
X = Cl,Br

In the foregoing Scheme D is outlined a route for the preparation of the intermediate amines (e) wherein $R_2$ is aryl and $R_1$, $R_3$, and $R_4$ are hydrogen. An appropriately substituted ω-halo acetophenone or propiophenone or butyrophenone (a) is reacted with a secondary amine in a manner similar to that described for Scheme A to produce an ω-aminoaceto- or propiophenone or butyrophenone (b).

Alternatively, to obtain the β-aminopropiophenone (b) a Mannich reaction may be carried out employing the desired secondary amine, formaldehyde and acetophenone (c). A protected amine may be employed similar to that described in Scheme C. The ω-aminoketone (b) is converted to the oxime (d) by reaction with hydroxylamine hydrochloride in an aqueous base or buffered solution. The oxime (d) is reduced to the diamine (e) by hydrogenation over platinum oxide or palladium on carbon in the presence of acid at about 30-50 psi or by chemical reduction utilizing tin in hydrochloric acid, lithium aluminum hydride, etc.

The foregoing Scheme E is illustrative of a method for the preparation of intermediate amines of the invention wherein $R_3$ is aryl, $R_1$, $R_2$ are H and n is the integer 0.

An ω-haloacetophenone (a) is reacted with sodium azide in a solvent such as dimethylformamide, ethanol, methanol, acetone/water or acetonitrile at a temperature of about 20°-120° C. to provide the corresponding ω-azidoacetophenone (b). Reductive amination of (b) under Borch conditions using sodium cyanoborohydride and a secondary amine in dry methanol provides an aminoazide (c). Again as described in the previous schemes, protected amines may be utilized. The azido group of (c) is reduced to the primary amine by reaction with lithium aluminum hydride under conditions outlined in Scheme C.

Scheme E

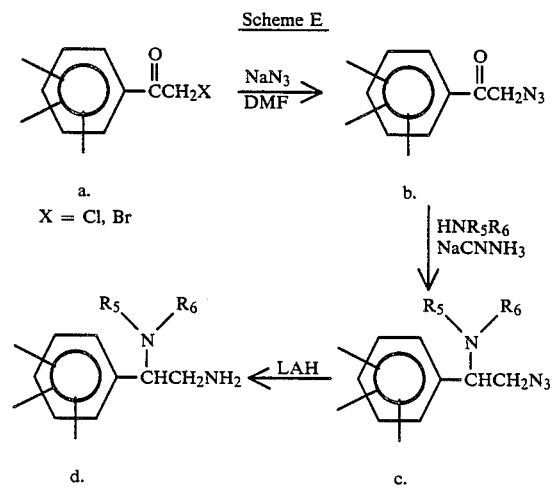

a.
X = Cl, Br

Scheme F

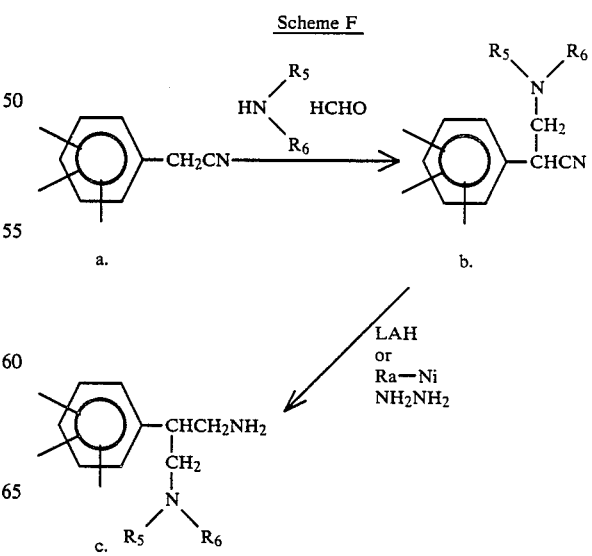

Scheme F illustrates the method for preparing intermediate amines of the invention wherein $R_3$ is aryl, $R_1$ and $R_2$ are hydrogen and n is the integer 1. Mannich reaction of a phenylacetonitrile (a) with formaldehyde and a secondary amine affords an aminonitrile (b). Reduction of compound (b) to a diamine (c) can be carried out with either lithium aluminum hydride or by reaction with hydrazine in aqueous ethanol in the presence of Raney nickel. The reaction with hydrazine is carried out at a temperature of 20° C.–80° C., preferably at about 50° C.–60° C.

Certain of the compounds of the invention contain asymmetric carbon atoms and as such may be prepared as their optically active or racemic components. Preparation of enantiomerically pure materials may be accomplished where necessary either by resolution of the racemate using an optically active acid, such as (+) tartaric acid, (−) camphorsulfonic acid, etc. or by resolution of one of the intermediate amines or diamines in a similar manner then completion of the synthesis with enantiomerically pure intermediates. Alternately, chiral synthetic techniques may be employed.

Method-Of-Use and Pharmaceutical Composition Aspect

The novel substituted 4-[1H-imidazol-1-yl]benzamides of this invention and their pharmaceutically acceptable salts are antiarrhythmic agents. These compounds are useful in the treatment of a variety of cardiac arrhythmias, more especially, these compounds, dependent on substituent design, will be useful as Class III or as a combination Class I/III antiarrhythmic agents. The combination Class I/III group contains those therapeutic effects attributed to Class I and Class III agents singly.

Those compounds within Formula I wherein $R_1$, $R_2$ or $R_3$ is aryl in nature—(e.g. phenyl, substituted phenyl, phenylalkyl, substituted phenylalkyl, naphthalenyl, substituted naphthalenyl) display the combination Class I/III activity. The other compounds of Formula I contain Class III activity singly.

In 1970, Vaughan Williams devised his, by now well known, method for classifying various antiarrhythmic agents. Generally speaking, Class I agents typified for example by flecainide, lidocaine or mexiletine are local anesthetics on nerve and myocardial membranes thereby slowing conduction which decreases the propagation of ectopic (premature) beats and suppresses the tendency of damaged cells to initiate ectopic beats. The Class II agents are the so-called β-blockers best exemplified by propranolol. The Class III agents represented by bretylium or amiodarone have little or no effect on conduction, in fact, they are quite independent of conduction. They prolong the action potential duration of the heart cells thus increasing the time interval in which the heart cells are unexcitable (refractory period) without slowing conduction or changing the excitability of the cardiac cells.

With the availability of such drugs the medical community dealing with cardiovascular abnormalities has a large armamentarium from which to choose the therapy needed for a given situation. Generally, after a myocardial infarct the patient is treated with a Class I agent because cardiac cells in the border zone of the infarcted region of the heart are electrically unstable, giving rise to ectopic beats resulting in the appearance of numerous PVC's (premature ventricular contractions). As the patients' infarct heals the tissue substrate for arrhythmia may change and potentially a re-entrant pathway may be established leading to ventricular tachycardias - which condition may be treated with a Class III agent. However, there are numerous instances when the physician must deal with patients whose treatment would call for the use of both a Class I and Class III agent. Recent clinical experience has demonstrated that combinations of certain antiarrhythmic agents may yield greater efficacy than if each is used alone, as for example, the enhanced response of patients to combinations of drugs during programmed electrical stimulation studies in the clinical setting. However, use of two agents potentially increases the possibilities of problems in multiple drug therapy, (e.g. side effects, metabolic problems, drug interactions, etc.) and the problems in patient compliance—different drugs, different therapeutic regimens.

The compounds of this invention provide the physician with chemical entities evoking a Class III response or those evoking a combination Class I/III response.

The compounds of the invention were tested in several biological procedures to analyze their type of antiarrhythmic effect. For instance, utilizing standard electrophysiological techniques, the resting potential, amplitude, duration, rate of rise of phase 0 (depolarization) of the action potential were measured in normal canine Purkinje fibers. Those compounds (for example, N-[2-(diethylamino)-ethyl]-4-(1H-imidazol-1-yl)-benzamide) which in this screen demonstrated an increase in action potential duration without a decrease in the rate of rise of phase 0 were designated Class III antiarrhythmic agents.

Those compounds as for instance N-[2-(diethylamino)ethyl]-4-(1H-imidazol-1-yl)-N-(1-naphthalenyl)benzamide which decreased the rate of rise of phase 0 (i.e., slowed conduction - the attribute of a Class I agent) in conjunction with increasing the action potential (an attribute of a Class III agent) were designated as combination Class I/III antiarrhythmic agents. These latter compounds with their combination effect vitiate the need for 2 compound therapy. Thus there is provided by this invention a method for treating arrhythmias which comprises administering to a subject suffering from arrhythmias and in need of treatment or to a subject suspected of developing said arrhythmias an effective amount for treating such arrhythmias of a compound of this invention. The compounds are preferably utilized for the control of those arrhythmias most generally treated with Class III or a combination Class I/Class III type antiarrhythmic agent.

In general, the compounds of this invention may be administered orally or parenterally. The dosage administered will be dependent on the subject being treated, the route of administration and the type and severity of the arrhythmias being prevented or reduced.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention for example, N-[2-(diethylamino)ethyl]-4-(1H-imidazol-1-yl)benzamide dihydrochloride in the amount of about 1 to about 500 mg. Such formulation can be administered orally at the dose of about 1 to 4 capsules per day or more often as needed, depending upon the particular condition and subject being treated. For parenteral administration a compound of this invention can be formulated as an intramuscular or intravenous medicament but is not limited thereto. In the case of treatment of a patient suffering from severe cardiac arrhythmias, it may be desirable to administer a compound of the invention by intravenous slow bolus in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or a saline solution, buffered aqueous solutions as well as dispersing and surface active agents if necessary. A typical formulation suited to intravenous or intramuscular administration may contain one of the compounds of this invention such as N-[2-(diethylamino)ethyl]-4-(1H-imidazol-1-yl)benzamide dihydrochloride or N-[2-(diethylamino)ethyl]-4-(1H-imidazol-1-yl)-N-(1-naphthalenyl)benzamide in the amount of about 50 to 150 mg and a solubilizing agent and sufficient sterile water to bring the volume to about 5 ml–100 ml. Such formulation can be infused at a constant rate or injected one to four times per day or more often depending upon the particular condition of the subject being treated.

It is further contemplated that the compounds of this invention may be formulated into sublingual lozenges or impregnated into fabric appliques for a type of transdermal application.

The pharmaceutical formulations of the compounds of this invention may optionally, additionally contain one or more other pharmaceutically active substances. As for instance combining the compounds of this invention with -adrenergic blocking agents for the treatment of mammalian subjects who have suffered myocardial infarction.

The invention described hereinabove is illustrated below in the Preparations and Examples, which, however, are not to be construed as limiting the scope of this invention.

PREPARATIONS

Preparation 1

1-(4-Fluorobenzoyl)-3-methylpiperazine

Add 25.0g (0.158 mol) of p-fluorobenzoyl chloride drop-wise to a 0° C. solution of 15.0 g (0.150 mol) of N-methylpiperazine and 20.0 g (0.189 mol) of sodium carbonate in 100 mL of water. Stir the resultant solution at 0° C. for about 30 minutes, then at room temperature for about 2 hr. Extract the resultant solution with methylene chloride (2×100 mL). Dry the combined extracts with $Na_2SO_4$ and evaporate the solvent to give the title compound.

NMR ($CDCl_3$): $\delta = 2.33(s,3)$, 2.40–2.58(m,4), 3.48–3.85 (m,4), and 6.95–7.58(m,4)ppm.

Preparation 2

N-[(1-Ethylpyrrolidin-2-yl)methyl]-4-fluorobenzamide

Add 5.05 g (31.8 mmol) of p-fluorobenzoyl chloride drop-wise to a 0° C. solution of 4.08 g (31.8 mmol) of 1-ethyl-2-(aminomethyl)pyrrolidine and 3.85 (35.0 mmol) of sodium carbonate in 50 mL of water. Stir the resultant solution at 0° C. for about 30 minutes, then at room temperature for about 20 hr. Extract the resultant solution with methylene chloride (2×100 mL). Dry the combined extracts with $Na_2SO_4$ and evaporate the solvent to give the title compound.

NMR ($CDCl_3$): $\delta = 1.13(t,3)$, 1.60–4.30(m,11), 6.87–7.37 (m,2), and 7.70–8.00(m,3)ppm.

Preparation 3

N-[2-(Diethylamino)ethyl]-4-fluorobenzamide

Add 24.4 g (0.154 mol) of p-fluorobenzoyl chloride in 100 mL of tetrahydrofuran dropwise to 17.88 g (0.154 mol) of N,N-diethylethylenediamine in 150 mL of tetrahydrofuran at 0° C. Stir at 0° C. for about 2 hr then at room temperature for about 17 hr. Concentrate the resultant solution and treat the residue with 1N NaOH until about pH=10. Extract the resultant solution with methylene chloride (2×100 mL). Dry the extract with $Na_2SO_4$ amd evaporate the solvent to give the title compound.

NMR (DMSO): $\delta = 0.97(t,6)$, 2.50(m,6), 3.32(q,2), 7.29 (t,2), 7.91(dd,2), and 8.45(t,1) ppm.

Preparation 4

In a manner similar to Preparation 3 the following compounds are prepared:
(a) p-fluorobenzoyl chloride +N,N,N'-triethyl1,2-ethanediamine =N-[2-(diethylamino)ethyl]N-ethyl-4-fluorobenzamide,
(b) p-fluorobenzoyl chloride+N-ethyl-N-heptyl1,2-ethanediamine=N-[ethyl(heptyl)amino]ethyl]-4-fluorobenzamide, and
(c) p-fluorobenzoyl chloride +N,N-dibutyl-1,2 ethanediamine =N-[2-(dibutylamino)ethyl]-4-fluorobenzamide.

Preparation 5

4-(1H -Imidazol-1-yl)benzoic acid methyl ester

Heat 101.6 g (0.65 mol) of methyl 4-fluorobenzoate, 66.65 g (0.98 mol) of imidazole, and 182.0 g (1.31 mol) of potassium carbonate in dimethylsulfoxide at ca. 120° C. for about 3 hr. Cool the solution to room temperature and pour into 500 mL of cold water. Filter to obtain crystals of the title compound.

NMR ($CDCl_3$): $\delta = 4.00(s,3)$, 7.30(m1), 7.40(m1), 7.45(d,2), 7.95(m1), and 8.20(d,2) ppm.

Preparation 6

N-(2-Aminoethyl)-4-(1H-imidazol-1-yl)benzamide hydrochloride

Heat 21.0 g (97.0 mmol) of methyl 4-(1H-imidazol-1-yl)-benzoate and 150 mL ethylenediamine at reflux for about 17 hr. Cool the solution to room temperature and remove the solvent. Dissolve the residue in ethanol (250 mL) and pass hydrochloric acid gas through the solution. Collect crystals of the title compound.

NMR (DMSO) $\delta = 3.02(t,2)$, 3.57(quar,2), 7.15(s,1), 7.81(d,2), 7.88(s,1), 8.11(d,2), 8.42(s,1), 8.99(t,1), and ca. 8.35 (br s,3)ppm.

Preparation 7

N-[2-(Diethylamino)ethyl]-4-fluoro-N-(1-napthalenyl)-benzamide

A solution of 8.0 g (33 mmol) of N,N-diethyl-N'-naphthalenyl-1,2-ethanediamine in 100 mL of tetrahydrofuran is treated with a solution of 6.8 g 4-fluorobenzoyl chloride in 50 mL of tetrahydrofuran and stirred at room temperature. After one hour, the solvent is evaporated on the rotary evaporator. The residue is dissolved in 200 mL of methylene chloride and washed with 200 mL of water and 4N sodium hydroxide to pH=14. The organic layer is dried over sodium sulfate, filtered and the solvent evaporated to provide the title compound.

NMR (CDCl$_3$): δ=1.05(t,6), 2.62(quar,4), 2.90(m,2), 3.86m,1), 4.58m,1), 6.70(t,2), 7.25(m,3), 7.33(t,1), 7.60(m,2), 7.78(d,1), 7.90(d,1) and 8.04(d,1) ppm.

Preparation 8

In a manner similar to Preparation 7 the following compounds may be prepared:
(a) N,N-diethyl-N'-phenyl-1,2-ethanediamine+4-fluorobenzoyl chloride=N-[2-(diethylamino)-ethyl]-4-fluoro-N-phenylbenzamide,
(b) N,N-diethyl-N'-(4-methylphenyl)-1,2-ethanediamine+4-fluorobenzoyl chloride =N-[2-(diethylamino)-ethyl]-4-fluoro-N-(4-methylphenyl)-benzamide,
(c) N,N-diethyl-N'-(4-methoxyphenyl)-1,2-ethanediamine+4-fluorobenzoyl chloride=N-[2-(diethylamino)ethyl]-4-fluoro-N-(4-methoxyphenyl)-benzamide, and
(d) N'-(4-chlorophenyl)-N,N-diethyl-1,2-ethanediamine+4-fluorobenzoyl chloride =N-(4-chlorophenyl)-N-[2-(diethylamino)ethyl]-4-fluorobenzamide.
(e) N,N-diethyl-N'(phenylmethyl)-1,2-ethanediamine+4-fluorobenzoyl chloride=N-[2-(diethylamino)-ethyl]-4-fluoro-N-(phenylmethyl)benzamide.
(f) N,N-diethyl-N'-(phenylmethyl)-1,2-cyclohexanediamine+4-fluorobenzoyl chloride =N-[2-(diethylamino)cyclohexyl]-4-fluoro-N-(phenylmethyl)-benzamide.

Preparation 9

3-[(Diethylamino)propyl]-4-fluorobenzamide

To 50 mL of THF at 0° C is added 13 g (85 mmol) of 4-fluorobenzoyl chloride and 11.5 g (89 mmol) of N,N-diethyl1,3-propanediamine. Warm the reaction to room temperature and stir overnight. Upon completion remove the solvent in vacuo and add 2N NaOH and CH$_2$Cl$_2$. Separate the organic layer and dry over Na$_2$SO$_4$. Filter the drying agent and remove the solvent in vacuo to obtain the title compound.

NMR (CDCl$_3$) δ=1.0(t,6), 1.7(m,2), 2.55(quar, 4), 2.6(m,2) 3.5(m,2), 7.0(dd,2), 7.75 (dd,2), and 8.7(br,1)ppm.

Preparation 10

3-Chloro-N-(2-phenylethyl)butaneamide

Dissolve 50 g (0.41 mol) of 3-chlorobutanoic acid in 500 mL of thionyl chloride. Reflux the mixture for ca. 12 hr. After this time remove the excess thionyl chloride in vacuo to obtain the crude 3-chlorobutanoic acid chloride. Dissolve the acid chloride in 100 mL of methylene chloride and add this solution dropwise to a cold (−10° C. -0° C.) stirring solution of 49.4 g (0.41 mol) of benzeneethanamine and 32.4 g (0.41 mol) of pyridine in 500 mL of methylene chloride. Maintain the temperature of the reaction mixture below 0° during the addition then stir the reaction at room temperature overnight. After this time wash the reaction mixture with 2×100 mL of 1N aqueous hydrochloric acid, 2×100 mL of saturated sodium bicarbonate solution and 100 mL of saturated sodium chloride solution. Dry the organic phase over anhydrous sodium sulfate. Remove the drying agent and evaporate the solvent to obtain the title compound.

Preparation 11

3-[Ethyl(heptyl)amino]-N-(2-phenylethyl)butaneamide

Reflux 5.0 g (21 mmol) of 3-chloro-N-[2-phenylethyl]butanamide, 3.0 gm (21 mmol) N-ethylheptanamine and 3.0 g (21 mmol) of potassium carbonate in 100 mL of methanol. Follow the progress of the reaction by thin layer chromatography on silica gel. At the completion of the reaction remove the solvent in vacuo and add 100 mL of H$_2$O. Extract the aqueous mixture with 3×100 mL of methylene chloride. Dry the organic extracts over anhydrous sodium sulfate. Remove the drying agent and evaporate the solvent to obtain the title compound.

Preparation 12

N$^3$-Ethyl-N$^3$-heptyl-N$^1$-(2-phenylethyl)-1,3-butanediamine

Dissolve 3.0 g (9 mmol) of 3-[ethyl(heptyl)amino]-N-(2-phenylethyl)butanamide in 50 mL of anhydrous tetrahydrofuran. Add this solution dropwise to a suspension of 0.68 g (18 mmol) of lithium aluminum hydride in 20 mL of anhydrous tetrahydrofuran under a nitrogen atmosphere. After the addition is complete heat the reaction mixture to reflux. Follow the progress of the reaction by thin layer chromatography on silica gel. At the completion of the reaction add successively dropwise 0.7 mL of water, 0.7 mL of 15% aqueous sodium hydroxide solution and 2.1 mL of water. Filter the resulting solids and wash with 20 mL of tetrahydrofuran. Evaporate the solvent in vacuo and dissolve the residue in 100 mL of methylene chloride. Wash the methylene chloride solution with 20 mL of water and 20 mL of saturated sodium chloride solution then dry over anhydrous sodium sulfate. Remove the drying agent and evaporate the solvent to obtain the title compound.

Preparation 13

N-[3-[Ethyl(heptyl)amino]butyl]-4-fluoro-N-(2-phenylethyl)benzamide

In a manner similar to Preparation 7 react N$^3$-ethyl-N$^3$-ethyl-N$^1$-heptyl-N'-(2-phenylethyl)-1,3-butanediamine with 4-fluorobenzoyl chloride to obtain the title compound.

EXAMPLES

Example I

1-[4-(1H-Imidazol-1-yl)benzoyl]-4-methylpiperazine dihydrochloride

Add 3.0 g (13.5 mmol) of 1-(4-fluorobenzoyl)-4-methylpiperazine to 10 mL of dimethylsulfoxide and add this via cannula to a solution of 1.38 g (20.3 mmol) of imidazole and 0.45 g (18.9 mmol) of sodium hydride in 10 mL of dimethylsulfoxide. Heat the resultant solution at ca. 125° C. for about 34 hr. Cool the solution to room temperature and pour into 100 mL of water. Extract the resultant solution with ethyl acetate+ethanol, 95+5 (2×100 mL). Dry the combined extracts with Na$_2$SO$_4$ and evaporate the solvent. Dissolve the residue in ethanol (50 mL) and pass hydrochloric acid gas through the solution until about pH=1. Concentrate the solution to obtain the title compound.

NMR (D$_2$O): δ–3.03(s,3), 3.31-3.73(m,8), 7.70(s,1), 7.75–7.85(m,4), 7.98(s,1), and 9.27 (s,1)ppm.

Example II

N-[(1-Ethylpyrrolidin-2-yl)methyl]- 4 (1H-imidazol-1-yl)-4-methylbenzenesulfonic acid salt Dissolve 5.8 g (23.2 mmol) of N-[(ethylpyrrolidin-2-yl)methyl]-4-fluorobenzamide in 5 mL of dimethylsulfoxide and add this via cannula to a solution of 2.37 g (34.8 mmol) of imidazole and 0.78 g (32.5 mmol) of sodium hydride in 15 mL of dimethylsulfoxide. Heat the resultant solution at ca. 125° C. for about 17 hr. Cool the solution to room temperature and pour into 200 mL of water. Extract the resultant solution with ethyl acetate +ethanol, 95+5 (2×100 mL). Dry the combined extracts with $Na_2SO_4$ and evaporate the solvent. Dissolve the residue in ethanol (50 mL) and treat with 3.19 g of 4-methylbenzenesulfonic acid. Evaporation of the solvent gives the title compound.

NMR ($D_2O$): δ–1.40(t,3), 1.62–2.38(m,4), 2.38(s,3), 2.62–2.77(m,2), 2.97–3.28(m,5), 7.23 (s,1), 7.35(d,2), 7.63–7.69(m,5), 7.92(d,2) and 8.23(s,2)ppm.

Example III

N-[2-(Diethylamino)ethyl]-4-(1H-imidazol-1-yl)benzamide dihydrochloride

Heat a mixture of 36.7 g (154.0 mmol) N-[2-(diethylamino)ethyl]-4-fluorobenzamide, 12.6 g (185.0 mmol) of imidazole, and 42.6 g (308.0 mmol) of potassium carbonate in 50 mL of dimethylsulfoxide at ca. 125° C. for about 44 hr. Cool the solution to room temperature and pour into 500 mL of water. Extract the resultant solution with methylene chloride (3×200 mL). Combine the organic extracts, dry with $Na_2SO_4$ and evaporate the solvent. Dissolve the residue in ethanol (100 mL) and add concentrated hydrochloric acid until about pH=1. Concentrate the solvent to give crystals of the title compound.

NMR (DMSO): δ—1.26(t,6), 3.20(m,4), 3.27(m,2), 3.50 (br s,1), 3.71(quar,2), 7.93(s,1), 7.97(d,2), 8.23(d,2), 8.39(,1), 9.36 (t,1), 9.83(s,1), and 10.80 (br s,1) ppm.

Example IV

In a manner similar to Example III the following compounds are prepared:
(a) N-[2-(diethylamino)ethyl]-N-ethyl-4-fluorobenzamide+1H-imidazole=N-[2-(diethylamino)-ethyl]-N-ethyl-4-(1H-imidazol-1-yl)benzamide,
(b) N-[2-[ethyl(heptyl)amino]ethyl]-4-fluorobenzamide+1H-imidazole =N-[2-[ethyl(heptyl)amino]ethyl]-4-(1H-imidazol-1-yl)benzamide, and
(c) N-[2-(dibutylamino)ethyl]-4-fluorobenzamide+1H-imidazole=N-[2-(dibutylamino)ethyl]-4-(1H-imidazol-1-yl)benzamide,
(d) N-[2-(diethylamino)ethyl]-4-fluoro-N-(phenylmethyl)benzamide+1H-imidazole =N-[2-(diethylamino)ethyl]4-(1H-imidazol-1-yl)-N-(phenylmethyl)benzamide,
(e) N-[2-(diethylamino)cyclohexyl]-4-fluoro-N-(2-phenylmethyl)benzamide+1H-imidazole =N-[2-(diethylamino)cyclohexyl]-4-(1H-imidazol-1-yl)-N-(phenylmethyl)benzamide,
(f) N-[3-[ethyl(heptyl)amino]butyl]-4-fluoro-N-(2-phenylethyl)benzamide+1H-imidazole =N-[3-[ethyl-(heptyl)amino]butyl]-4-(1H-imidazol-1-yl)-N-(2-phenylethyl)benzamide.

Example V

N-[2-(Diethylamino)ethyl]-4-(1H-imidazol-1-yl)benzamide dihydrochloride

Heat 5.0 g (25.0 mmol) of 4-(1H-imidazol-1-yl)benzoic acid methyl ester and 2.89 g (25.0 mmol) of N,N-diethyl-1,2-ethanediamine in 15 mL of xylenes at reflux for about 48 hr. Cool the solution to room temperature and remove the solvent. Treat the residue with 10% aq. sodium hydroxide solution (50 mL) and extract with methylene chloride (2×25 mL). Combine the organic extracts, dry with $Na_2SO_4$, and evaporate the solvent. Dissolve the residue in ethanol (50 mL) and treat with concentrated hydrochloric acid until about pH=1. Evaporate the solvent to give the title compound.

NMR (DMSO): δ=1.26(t,6), 3.20(m,4), 3.27(m,2), 3.50(br s,1), 3.71(quar,2), 7.93 (s,1), 7.97(d,2), 8.23(d,2), 8.39 (s,1), 9.36(t,1), 9.83(s,1) and 10.80(br s,1)ppm.

Example VI

N-[2-[Bis-(phenylmethyl)amino]ethyl]-4-(1H-imidazol-1-yl)-benzamide hemihydrate Heat 4.23 g (21.0 mmol) of 4-(1H-imidazol-1-yl)benzoic acid methyl ester and 5.00 g (21.0 mmol) of N,N-dibenzylethylenediamine in 10 mL of xylenes at reflux for about 48 hr. Cool the solution to room temperature. Filter to obtain crystals of the title compound.

NMR ($CDCl_3$): δ=2.73(t,2), 3.50(quar,2), 3.64(s,4), 6.50(br s,1), 7.24–7.42(m,12), 7.46 (d,2), 7.72(d,2) and 7.95(s,1)ppm.

Example VII

N-[2-[(Phenylmethyl)amino]ethyl]-4-(1H-imidazol-1-yl)-benzamide hydrochloride Suspend 4.0 g (9.7 mmol) of N-[2-[bis-(phenylmethyl)amino] ethyl]-4-(1H-imidazol-1-yl)benzamide hemihydrate in methanol (25 mL) and treat with 7.0 mL of 1.35 M hydrochloric acid in methanol and 0.5 g of 10% palladium on carbon. Hydrogenate the mixture at ca. 19 psi for about 17 hr. Filter the mixture through celite and evaporate the filtrate. Triturate the residue with ethanol to give crystals of the title compound.

NMR (DMSO): δ=3.13(t,2), 3.65(quar, 2), 4.21(s,2), 7.15(s,1), 7.41–7.60(m,5), 7.81(d,2), 7.87(s,1), 8.06(d,2), 8.41(s,1), 8.97 (t,1) and 9.40(br s,2)ppm.

Example VIII

Trans-N-[2-(diethylamino)cyclohexyl]-4-(1H-imidazol-1-yl)-benzamide hydrochloride Trimethylaluminum (42.0 mmol) is added dropwise to a solution of trans-N,N-diethyl-1,2-cyclohexanediame (6.91 g, 40.6 mmol) in 90 mL of $CH_2Cl_2$. The mixture is heated at 55° C. for 20 min. A solution of methyl 4-(1H-imidazol-1-yl)benzoate (9.0 g, 44.5 mmol) in 90 mL of $CH_2Cl_2$ is prepared and added dropwise, and the mixture is refluxed for several days under a nitrogen atmosphere. The cooled mixture is quenched with saturated $NH_4Cl$ solution and extracted at pH=11 with $CH_2Cl_2$. The combined organic portions are washed with brine and dried with $Na_2SO_4$. Removal of the solvent under reduced pressure yields the product as a yellow oil which is converted to the hydrochloride salt. Recrystallization from 5% MeOH/ acetone produces a white crystalline solid.

NMR (DMSO): δ=1.20–1.40(m,7), 1.50–1.80 m,3), 1.80–2.00(m,2), 2.10–2.20m,1), 2.95–3.10 m,1), 3.10–3.25m,1), 3.38–3.60(m,4+H20), 4.25–4.40m,1), 7.19(s,1), 7.85(d,2), 7.92(s,1), 8.14(d,2), 8.46 (s,1), 8.55–8.70m,1) and 8.80(d,1) ppm.

Example IX

N-[2-(Diethylamino)ethyl]-4-(1H-imidazol-1-yl)-N-(1naphthalenyl)benzamide

A mixture of 6.0 g (16.5 mmol) N-[2-(diethylamino)ethyl]-4-fluoro-N-(1-naphthalenyl)benzamide, 1.68 g (24.7 mmol) of imidazole, 4.55 g (33 mmol) of anhydrous potassium carbonate and 6.0 mL of dimethylsulfoxide is heated to 150° C. for 18 hr. After this time, the reaction mixture is dissolved in 150 mL water, 100 mL methylene chloride and 40 mL of methanol. The organic is dried over sodium sulfate, filtered and the solvent distilled in vacuo. The residue is recrystallized from acetone to provide the title compound.

NMR (DMSO): δ=0.90(t,6), 2.43(quar,4), 2.67(m,2), 3.56m,1), 4.33m,1) 7.01(s,1), 7.32(d,2), 7.39(d,2), 7.43(m,2), 7.58(t,1), 7.64(s,1), 7.65(t,1), 7.83(d,1), 7.97(d,1), 8.04(d,1) and 8.17(s,1)ppm.

Example X

In a manner similar to Example IX the following compounds may be prepared:
(a) N-[2-(diethylamino)ethyl]-4-fluoro-N-phenylbenzamide + 1H-imidazole = N-[2-(diethylamino)ethyl]-4-(1H-imidazol-1-yl)-N-phenylbenzamide,
(b) N-[2-(diethylamino)ethyl]-4-fluoro-N-(4-methylphenyl)benzamide + 1H-imidazole = N-[2-(diethylamino)ethyl]-4-(1H-imidazol-1-yl)-N-(4-methylphenyl)benzamide,
(c) N-[2-(diethylamino)ethyl]-4-fluoro-N-(4-methoxyphenyl)benzamide + 1H-imidazole = N-[2-(diethylamino)ethyl]-4-(1H-imidazol-1-yl)-N-(4-methoxyphenyl)benzamide, and
(d) N-(4-chlorophenyl)-N-[2-(diethylamino)ethyl]-4-fluorobenzamide + 1H-imidazole = N-(4-chlorophenyl)-N-[2-(diethylamino)ethyl]-4-(1H-imidazol-1-yl)benzamide.

Example XI

N'-[3-(Diethylamino)propyl]-4-(1H-imidazol-1-yl)benzamide dihydrochloride

To 50 mL of DMSO is added 19.5 g (77 mmol) of N-[3-(diethylamino)propyl]-4-fluorobenzamide, 8 g (0.12 mol) of 1H-imidazole, and 11 g (80 mmol) of $K_2CO_3$. Heat the reaction at 170° C. for 1 day then add 300 mL of $H_2O$ and extract with $CH_2Cl_2$. Wash the organic layer with $H_2O$ and dry the organic phase over $Na_2SO_4$. Remove the drying agent by filtration and remove solvent in vacuo. Dissolve resulting oil in methanol and add concentrated HCl. Remove the solvent in vacuo and recrystallize solid from isopropanol - methanol to obtain the title compound.

NMR (DMSO-$d_6$): δ=1.24(t,6), 2.0(m,2), 3.1(m,6), 3.4 (dt,2), 7.94(s,1), 7.98(d,2), 8.18 (d,2), 8.39(s,1), 9.08(t,1), 9.81 (s,1) and 10.6(br,1)ppm.

Contemplated as equivalents to the compounds of this invention are those of the following Formulae VII and VIII.

VII $$\text{N} \diagdown\diagup \text{N}-\text{C}_6\text{H}_4-\overset{O}{\underset{\|}{C}}-O-\overset{R_2}{\underset{|}{C}}\text{H}-\overset{R_3}{\underset{|}{C}}\text{H}(CH)_n-\overset{R_4}{\underset{|}{}}\text{N}\diagup^{R_5}_{R_6}$$

and

VIII $$\text{N} \diagdown\diagup \text{N}-\text{C}_6\text{H}_4-SO_2-\overset{R_1}{\underset{|}{N}}-\overset{R_2}{\underset{|}{C}}\text{H}-\overset{R_3}{\underset{|}{C}}\text{H}-(CH)_n-\overset{}{\underset{R_4}{}}\text{N}\diagup^{R_5}_{R_6}$$

wherein $R_1$, $R_2$, $R_3$, $R_4$, $R_5$, $R_6$ and the pharmaceutically acceptable salts take the same meaning as in Formula I.

Formulae VII and VIII are exemplified by 4-(1H-imidazol-1-yl)benzoic acid 2-(diethylamino)ethyl ester and N-(2-(diethylamino)ethyl)-4-(1H-imidazol-1-yl)benzenesulfonamide, respectively, which compounds are also to be construed as Class III or combination Class I/III antiarrhythmic agents.

We claim:

1. A compound of the formula I:

I $$\text{N} \diagdown\diagup \text{N}-\text{C}_6\text{H}_4-\overset{O}{\underset{\|}{C}}-\overset{R_1}{\underset{|}{N}}-\overset{R_2}{\underset{|}{C}}\text{H}-\overset{R_2}{\underset{|}{C}}\text{H}-\overset{R_3}{\underset{|}{C}}\text{H}-(CH)_n-\overset{}{\underset{R_4}{}}\text{N}\diagup^{R_5}_{R_6}$$

wherein:

$R_1$ is hydrogen, lower alkyl, lower alkenyl, lower alkoxy-lower alkyl, phenyl, substituted phenyl, naphthalenyl, substituted naphthalenyl, phenylalkyl, substituted phenylalkyl or collectively with $R_5$ may produce a piperazine or a hexahydro-1,4-diazepine ring system;

$R_2$ is hydrogen, lower alkyl, phenyl, substituted phenyl, naphthalenyl, substituted naphthalenyl or collectively with $R_3$ is a bond or an alkylene chain to form a saturated carbocyclic ring of from 4 to 8 ring carbons or collectively with $R_5$ is a alkylene chain to form a heterocyclic of from 5 to 8 ring members;

$R_3$ is hydrogen, lower alkyl, phenyl, substituted phenyl, naphthalenyl, substituted naphthalenyl, or collectively with $R_5$ is an alkylene chain to form a heterocyclic of from 5 to 8 ring members;

$R_4$ is hydrogen, methyl or ethyl;

$R_5$, $R_6$ are hydrogen, lower alkenyl, $C_1$–$C_8$ straight or branched chain alkyl, $C_3$–$C_6$ cycloalkyl, cycloalkyl(lower)alkyl, lower alkyl substituted by phenyl which may be substituted by up to 3 substituents selected from hydroxy or methoxy groups, or when taken together form a saturated heterocyclic ring of from 4 to 8 ring members which may be substituted by one or more methyl groups or optionally contain an $$-O-, \quad -\underset{R_7}{\underset{|}{N}}- \quad \text{or} \quad -\underset{\underset{O_p}{\Downarrow}}{S}- \quad \text{linkage}$$

where $R_7$ is a $C_1$–$C_8$ straight or branched chain alkyl or phenylalkyl wherein the phenyl group may be optionally substituted by up to three substituents selected from $C_1$–$C_4$ alkyl, $C_1$–$C_4$ alkoxy, trifluoromethyl, fluorine, chlorine and bromine;

p is the integer 0, 1, or 2;

n is the integer 0 or 1;
and the pharmaceutically acceptable salts thereof; with the provisos that:
 (a) only one of $R_1$, $R_2$ or $R_3$ can contain an aromatic substituent;
 (b) if one of $R_2$ or $R_3$ contains an aromatic substituent then the other plus $R_1$ and $R_4$ must be hydrogen;
 (c) $R_5$ and $R_6$ cannot both be hydrogen;
 (d) when any one of $R_1$, $R_5$ or $R_6$ is lower alkenyl, the unsaturation cannot be alpha to the carbon atoms;
and the pharmaceutically acceptable salts thereof.

2. A compound of claim 1 wherein n is 0 and $R_5$ and $R_6$ are both $C_1$–$C_8$ straight or branched chain alkyl.

3. A compound of claim 1 wherein n is 0 and $R_2$ collectively with $R_3$ is an alkylene chain to form a saturated carbocyclic ring of from 4 to 8 carbon atoms.

4. A compound of claim 1 wherein n is 0 and one of $R_1$, $R_2$ or $R_3$ is phenyl, substituted phenyl, naphthalenyl or substituted naphthalenyl.

5. A compound of claim 2 which is N-[2-(diethylamino)-ethyl]-4-(1H-imidazol-1-yl)benzamide.

6. A compound of claim 3 which is trans-N-[2-(diethylamino)cyclohexyl]-4-(1H-imidazol-1-yl)benzamide.

7. A compound of claim 4 which is N-[2-(diethylamino)-ethyl]-4-(1H-imidazol-1-yl)-N-(1-naphthalenyl)benzamide.

8. A compound of claim 1 which is 1-[4-(1H-imidazo-1-yl)benzoyl]-4-methylpiperazine.

9. A compound of claim 1 which is N-[(1-ethylpyrrolidin-2-yl)methyl]-4-(1H-imidazol-1-yl)benzamide.

10. A compound of claim 1 which is 4-(1H-imidazol-1-yl)-N-[2-bis-(phenylmethyl)amino]ethyl]benzamide.

11. A compound of claim 1 which is 4-(1H-imidazol-1-yl)-N-[2-[(phenylmethyl)amino]ethyl]benzamide.

12. A compound of claim 4 which is N-[2-(diethylamino)ethyl]-4-[1H-imidazol-1-yl]-N-(4-methoxyphenyl)benzamide.

13. The method of treating arrhythmias in a mammalian subject in need thereof comprising administering to said subject an antiarrhythmically effective dose of a compound according to claim 1.

14. A pharmaceutical composition for treating arrhythmias comprising an antiarrhythmic effective amount of a compound of claim 1 together with a nontoxic pharmaceutically acceptable carrier.

* * * * *

UNITED STATES PATENT AND TRADEMARK OFFICE
CERTIFICATE OF CORRECTION

PATENT NO. : 4,804,662

DATED : February 14, 1989

INVENTOR(S) : Klaus Nickisch, et al.

It is certified that error appears in the above-identified patent and that said Letters Patent is hereby corrected as shown below:

Column 1, line 30

"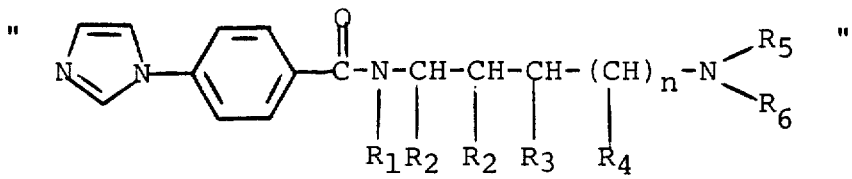"

should read

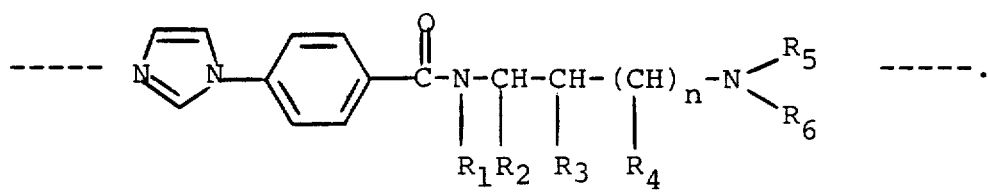 -----.

Column 2, line 43

"$C_1$-C8 straight" should read ----- $C_1$-$C_8$ straight -----.

Column 2, line 51

"$C_1$-C8 straight" should read ----- $C_1$-$C_8$ straight -----.

Column 3, line 35

"cylohexylmethyl" should read -----cyclohexylmethyl-----.

UNITED STATES PATENT AND TRADEMARK OFFICE
CERTIFICATE OF CORRECTION

PATENT NO. : 4,804,662

DATED : February 14, 1989

INVENTOR(S) : Klaus Nickisch, et al.

It is certified that error appears in the above-identified patent and that said Letters Patent is hereby corrected as shown below:

Column 5, line 55

"A illustrated" should read -----As illustrated-----.

Column 12, line 25

"triethyl1,2-" should read -----triethyl-1,2- -----.

Column 12, line 26

"ethyl]N-" should read -----ethyl]-N-----.

Column 12, line 27

"N-heptyl1,2-" should read -----N-heptyl-1,2- -----.

Column 12, lines 43 & 44

"7.30(ml), 7.40(ml)," should read -----7.30(m,1), 7.40(m,1)-----.

Column 13, line 6

"3.86m,1), 4.58m,1)," should read -----3.86(m,1), 4.58(m,1)-----.

Column 13, line 40

"N,N-diethyl1,3-" should read -----N,N-diethyl-1,3- -----.

Column 16, line 67

"1.50-1.80 m,3)," should read -----1.50-1.80(m,3),-----.

UNITED STATES PATENT AND TRADEMARK OFFICE
CERTIFICATE OF CORRECTION

PATENT NO. : 4,804,662

DATED : February 14, 1989

INVENTOR(S) : Klaus Nickisch, et al.

It is certified that error appears in the above-identified patent and that said Letters Patent is hereby corrected as shown below:

Column 16, line 68, 2.10-2.20m,1), should read 2.10-2.20 (m,1)

"2.95-3.10 m,1)," should read -----2.95-3.10(m,1),-----.

Column 17, line 1

"3.10-3.25m,1), 3.38-3.60(m,4+H$_2$O), 4.25-4.40m,1)," should read -----3.10-3.25(m,1), 3.38-3.60(m,4 + H$_2$O), 4.25-4.40(m,1),----.

Column 17, line 3

"8.55-8.70m,1)" should read -----8.55-8.70(m,1)-----.

Column 17, line 7

"(1naphthalenyl)" should read -----(1-naphthalenyl)-----.

Column 17, line 19

"3.56m,1), 4.33m,1)" should read -----3.56(m,1), 4.33(m,1)-----.

Column 18, line 11

"R$_5$, R$_6$ and the pharma..." should read R$_5$, R$_6$ and n and the pharma----.

Column 18, line 25

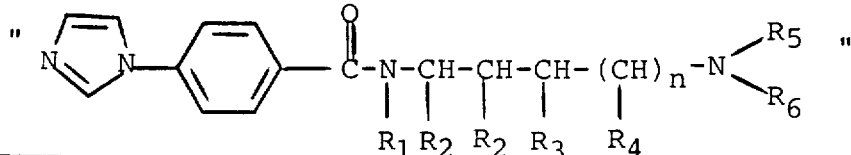

UNITED STATES PATENT AND TRADEMARK OFFICE
CERTIFICATE OF CORRECTION

PATENT NO. : 4,804,662

DATED : February 14, 1989

INVENTOR(S) : Klaus Nickisch, et al.

It is certified that error appears in the above-identified patent and that said Letters Patent is hereby corrected as shown below:

should read

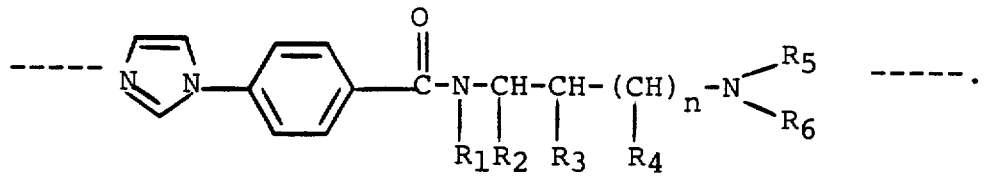

Column 20, line 4

"(1H-imidazo-" should read ----(1H-imidazol- -----.

Signed and Sealed this

Tenth Day of April, 1990

Attest:

HARRY F. MANBECK, JR.

Attesting Officer

Commissioner of Patents and Trademarks